US006458820B1

(12) United States Patent
Hall et al.

(10) Patent No.: US 6,458,820 B1
(45) Date of Patent: *Oct. 1, 2002

(54) METHOD FOR PREVENTING OR THE PROGRESSION OF NEURONAL DAMAGE WITH PRAMIPEXOLE AS A NEUROPROTECTIVE AGENT

(75) Inventors: Edward Dallas Hall, Portage; Philip F. Von Voigtlander, Plainwell, both of MI (US); Frank A. Rohde, Weiler (DE)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/706,535

(22) Filed: Nov. 3, 2000

Related U.S. Application Data

(60) Division of application No. 09/249,863, filed on Feb. 16, 1999, now Pat. No. 6,156,777, which is a division of application No. 08/849,831, filed on Jun. 10, 1997, now abandoned, and a division of application No. PCT/US95/15613, filed on Dec. 12, 1995, which is a continuation-in-part of application No. 08/357,121, filed on Dec. 15, 1994, now Pat. No. 5,650,420.

(51) Int. Cl.[7] ............................................. A68K 31/425
(52) U.S. Cl. ....................................... 514/367; 514/879
(58) Field of Search ................................ 514/367, 879

(56) References Cited

U.S. PATENT DOCUMENTS

| 4,843,086 A | | 6/1989 | Griss et al. ................... 514/425 |
| 4,886,812 A | | 12/1989 | Griss et al. ................... 514/321 |
| 5,112,842 A | | 5/1992 | Zierenberg et al. ........... 514/367 |
| 5,650,420 A | * | 7/1997 | Hall et al. ..................... 514/367 |
| 6,156,777 A | * | 12/2000 | Hall et al. ..................... 514/367 |

FOREIGN PATENT DOCUMENTS

| DE | 39 33 738 | 10/1989 | |
| DE | 38 43 227 | 7/1990 | |
| EP | 186087 | 8/1989 | ......... C07D/277/82 |
| EP | WO94/13287 | 6/1994 | |

OTHER PUBLICATIONS

Society for Neuroscience Abstracts, 19:673 (1993); id., at 1645.

Miya Zawa, et al. Nippon–Yakurigaku–Zasshi 98(6):449–561, (1991).

Ther–Pharmacol–Clin., vol. 11, issue 118, pp. 7–12 (1993).

* cited by examiner

*Primary Examiner*—Kevin E. Weddington
(74) *Attorney, Agent, or Firm*—Thomas A. Wootton; Austin W. Zhang

(57) ABSTRACT

The present invention provides the use of pramipexole as a neuroprotective agent.

5 Claims, No Drawings

METHOD FOR PREVENTING OR THE PROGRESSION OF NEURONAL DAMAGE WITH PRAMIPEXOLE AS A NEUROPROTECTIVE AGENT

CROSS-REFERENCE TO RELATED APPLICATIONS

This application is a division of application No. 09/249,863 filed on Feb. 16, 1999, U.S. Pat. No. 6,156,777, which is a division of application No. 08/849,831 filed on Jun. 10, 1997, abandoned, and a division of application No. PCT/US95/15613 filed Dec. 12, 1995, which is a continuation-in-part of application No. 08/357,121 filed Dec. 15, 1994, U.S. Pat. No. 5,650,420.

FIELD OF THE INVENTION

The present invention relates to the use of pramipexole or 2-amino-6-n-propylamino-4,5,6,7-tetrahydrobenzothiazole, or the (+)- or (−)-enantiomers thereof, and the pharmacologically acceptable salts thereof, as a neuroprotective agent.

BACKGROUND OF THE INVENTION

A number of central nervous system diseases and conditions result in neuronal damage. These conditions which can lead to nerve damage include:

Primary neurodegenerative disease; Huntington's Chorea; Stroke and other hypoxic or ischemic processes; neurotrauma; metabolically induced neurological damage; sequelae from cerebral seizures; hemorrhagic stroke; secondary neuro-degenerative disease (metabolic or toxic); Parkinson's disease; Alzheimer's disease, Senile Dementia of Alzheimer's Type (SDAT); age associated cognitive dysfunctions; or vascular dementia, multi-infarct dementia, Lewy body dementia, or neurodegenerative dementia.

Pramipexole is a dopamine-$D_3/D_2$ agonist the synthesis of which is described in European Patent 186 087 and its counterpart, U.S. Pat. No. 4,886,812. It is known primarily for the treatment of schizophrenia and Parkinson's disease. It is known from German patent application DE 38 43 227 that pramipexole lowers the plasma level of prolactin. Also, this European patent application discloses the use of pramipexole in the treatment of drug dependency. Further, it is known from German patent application DE 39 33 738 that pramipexole can be used to decrease abnormal high levels of thyroid stimulating hormone (TSH). U.S. Pat. No. 5,112,842 discloses the transdermal administration of the compounds and transdermal systems containing these active compounds. WO patent application PCT/EP 93/03389 describes the use of pramipexole as an antidepressant agent.

Up to now there is no commercially available drug for the therapeutic treatment of stroke with proven evidence of efficacy.

Surprisingly and unexpectedly, it has been found that pramipexole and its (+)-enantiomer also has a neuroprotective effect.

INFORMATION DISCLOSURE

Piribedil, a vasodilator which binds to a multitude of receptors including dopamine receptors, is reported to have an effect on functional and biochemical parameters in a gerbil model of global cerebral ischemia. See, e.g., Society for Neuroscience Abstracts, 19:673 (1993); id., at 1645.

Lisuride binds to several different receptors including dopamine $D_2$ and 5-HT1a receptors. It is reported that Lisuride, when administered before the event, reduced brain edema and prolonged survival time in a rat model of cerebral infarction. Miya Zawa, et al. Nippon-Yakurigaku-Zasshi 98(6):449–561, (1991).

SUMMARY OF THE INVENTION

The present invention particularly provides a method for preventing neuronal damage in a patient suffering from or susceptible to such neuronal damage comprising the administration of an effective amount of 2-amino-6-n-propylamino-4,5,6,7-tetrahydrobenzothiazole, its (−)-enantiomer or (+)-enantiomer thereof, and pharmacologically acceptable salts thereof especially an effective amount of pramipexole which is the (−)-enantiomer of 2-amino-6-n-propylamino-4,5,6,7-tetrahydrobenzothiazole-dihydrochloride or an effective amount of the (+)-enantiomer of 2-amino-6-n-propylamino-4,5,6,7-tetrahydrobenzothiazole dihydrochloride.

Conditions which can cause nerve damage are well-known to an ordinarily skilled neurologist or similar physician and include:

Primary neurogenerative disease;
Huntington's Chorea;
Stroke and other hypoxic or ischemic processes;
Neurotrauma;
Metabolically induced neurological damage;
Sequelae from cerebral seizures;
Hemorrhagic stroke;
Secondary neurodegenerative disease (metabolic or toxic);
Parkinson's disease;
Alzheimer's disease, other memory disorders; or
Vascular dementia, multi-infarct dementia, Lewy body dementia, or neurogenerative dementia.

The preferred indication for pramipexole, in the context of the present invention, is Parkinson's disease which is characterized by progressive degeneration of nigrostriatal dopamine neurons. In this sense, the term Parkinson's disease also comprises the term Parkinson's syndrome. In addition to pramipexole's palliative action (i.e. replacement of the lost dopamine neurotransmitter function), the compound may slow the degeneration of surviving dopamine neurons and thereby slows the progression of the disease.

The prophylactic use of the compound of this invention includes use as monotherapy in early or pre-symptomatic stages of Parkinson's disease and prevention of neurodegenerative disorders based on ischaemia.

The synthesis, formulation and administration of pramipexole is described in U.S. Pat. Nos. 4,843,086; 4,886,812; and 5,112,842; which are incorporated by reference herein.

2-Amino-6-n-propyl-amino-4,5,6,7-tetrahydrobenzothiazole, particularly the (−)-enantiomer thereof, and the pharmacologically acceptable acid addition salts thereof can be given for preventing of neuronal damage. The form of conventional galenic preparations consist essentially of an inert pharmaceutical carrier and an effective dose of the active substance; e.g., plain or coated tablets, capsules, lozenges, powders, solutions, suspensions, emulsions, syrups, suppositories, etc.

L-dopa is shown to be toxic to cerebellar granule cells in culture. Pramipexole and the (+) enantiomer blocked L-dopa toxicity. The $EC_{50}$ for both was between 0.3 and 1 uM and 10 uM provided viability measurements that were equal to control cells not exposed to L-dopa. The mechanism of protection does not appear to involve receptor activation given that the (+) enantiomer is less active in monoamine receptor binding assays. The possibility exists that 2-amino-6-n-propylamino-4,5,6,7-tetrahydrobenzothiazole, its (+) and (−) enantiomers and the pharmacologically acceptable acid addition salts thereof, especially pramipexole and the (+) enantiomer are acting as antioxidants toward reactive oxygen species known to be generated from L-dopa incubation.

The effective dose range is 0.01 to 2.0 mg/kg. More preferred is a dose of 1–2 mg/kg PO. The preferred total dose level for neuroprotection is 0.5–20 mg/kg/day PO. The preferred human dose is 0.1–6.0 mg/day total dose, divided in 2 or 3 administrations. In addition to being administered by oral or intravenous route, pramipexole may be administered transdermally.

DESCRIPTION OF THE PREFERRED EMBODIMENTS

The present invention is seen more fully by the examples given below:

EXAMPLE 1

We examined histologically retrograde degeneration of the dopaminergic nigrostriatal (NS) tract over 28 days in gerbils subjected to a 10-minute period of forebrain ischemia via bilateral carotid occlusion. There was in control animals a 39% loss of NS cell bodies in the zona compacta (as judged by tyroxine hydroxylase immunocytochemistry) over that time period. Daily post-ischemic oral dosing (1 mg/kg PO BID beginning at 1 hr after insult) with pramipexole attenuated 28-day post-ischemic loss of NS DA neurons by 36% (p<0.01 vs vehicle-treated).

EXAMPLE 2

We have successfully replicated the finding of Example 1; i.e., that pramipexole can protect nigrostriatal dopamine neurons in a gerbil model of 10 minutes of bilateral carotid occlusion-induced forebrain ischemia plus 28 days of post-ischemic survival. The administration of pramipexole was via an initial dose of 1 mg/kg PO 60 minutes after ischemia and again at the end of day 1 followed by twice daily dosing for the next 26 days. A twice daily dose of 0.3 mg/kg produced a threshold effect (14% increase in nigrostriatal dopamine neurons compared to vehicle). A twice daily dose of 1 mg/kg produced a significant 38% improvement in 28 day post-ischemic dopamine neuronal survival (p<0.0001 vs vehicle-treated). This action appears to be specific for dopamine neurons since the post-ischemic loss of the non-dopaminergic neurons in the CA1 area of the hippocampus was not significantly affected.

EXAMPLE 3

Primary Cultures of Cerebellar Granular Cells

Primary cultures of cerebellar granular cells were prepared from 8-day-old Sprague Dawley rats (Charles River, Portage, Mich.) as described previously (1). Neurons were grown on 6-well, 35 mm culture dishes (Nunc, Denmark) for 8–9 days, 2 ml/well, at a density of $1\times10^6$ cells/ml. Glial cell proliferation was prevented by adding cytosine-arabinofuranoside-monophosphate (Sigma, St. Louis, Mo.), 19 hrs after plating at a final concentration of $10\mu M$. Cultures generated by this method have been characterized and shown to contain more than 90% granule cells (2).

Cell Toxicity Models

Experiments were started after cells were 8 days in vitro (8 DIV). Cells were washed with two ml of serum free growth medium. Concentrations of 100X stock solutions of PPX and the (+) enantiomer in serum free growth medium were made. These were delivered to cells by adding 20 ul to cells in growth medium per well. The final concentration of drugs ranged from 1 nM to 10 uM. After 5 min 20 ul of a 10X stock solution of L-dopa in serum free growth medium was added to each well so that the final concentration was 100 uM. Cells were incubated under the above conditions for 24 hrs. For viability measurements cells were then washed twice and pulsed with 1 $\mu$Ci/ml of $\alpha$-(methyl)-$^{14}$C)-aminoisobutyric acid (New England Nuclear) in Locke's buffer for 1 hr. Cells were solubilized, following a wash, with 0.5% Triton X-100. The solubilized cells were then counted for radioactivity on a scintillation counter. Data was expressed as the mean of triplicates ±S.D. for each point.

Results from the table show that pramipexole was neuroprotective toward the toxicity (64.8%) associated with L-dopa. At 10 uM pramipexole, L-dopa treated cells were not different from controls. Pramipexole is shown to decrease slightly but significantly cAMP levels in cerebellar granular cells (3). This suggests the possible involvement of dopamine receptors ($D_2$ family) in the mechanism of neuroprotection.

To test this hypothesis, the (+) enantiomer was tested in a parallel experiment with pramipexole. The (+) enantiomer has been shown to be inactive in a battery of binding assays that involve adrenergic and serotonergic receptors, and less active in dopaminergic receptors. The results show that the (+) enantiomer is equally as potent and effective compared to pramipexole as a neuroprotective agent in this assay.

The neuroprotective effects of pramipexole in L-dopa mediated toxicity in cerebellar granule cell does not appear to involve the activation of dopamine receptors.

The (+) enantiomer of pramipexole shows utility as a neuroprotectant despite the fact that it shows little ability to bind to monoamine receptors.

The possibility exists that pramipexole and it's (+) enantiomer can act as an antioxidant toward L-dopa toxicity which is known to involve the generation of reactive oxygen species.

TABLE 1

Toxicity (64.8%) of 100 uM L-dopa:
Effects of pramipexole and (+) enantiomer.

| Dose (nM) | Pramipexole (% of control*) | (+) enantiomer (% of control*) |
|---|---|---|
| 0 | 35.2 +/− 8.5 | 35.2 +/− 8.5 |
| 1 | 30.0 +/− 6.5 | 51.3 +/− 5.8 |
| 10 | 39.2 +/− 9.4 | 57.8 +/− 4.9 |
| 100 | 64.8 +/− 4.7 | 58.3 +/− 10.3 |
| 300 | 76.2 +/− 7.3 | 81.0 +/− 18.3 |
| 1000 | 65.5 +/− 14.8 | 86.9 +/− 7.0 |
| 3000 | 84.9 +/− 0.6 | 95.2 +/− 2.5 |
| 10000 | 90.0 +/− 11.5 | 99.8 +/− 8.9 |

*Control is defined as the radioactivity associated with cells that were exposed to vehicle buffer rather than 100 uM L-dopa. Control value was equal to an average of 129547 CPMs for triplicate counts.

What is claimed is:

1. A method for preventing neuronal damage or the progression of neuronal damage in a patient suffering from or susceptible to such neuronal damage comprising the administration of an effective amount of a compound selected from the (−) enantiomer of 2-amino-6-n-propylamino-4,5,6,7-tetrahydrobenzo-thiazole, and pharmacologically acceptable acid addition salts thereof.

2. The method of claim 1, wherein said neuronal damage is caused by symptoms from the following diseases: Parkinson's disease, primary neurodegenerative disease; Huntington's Chorea; stroke and other hypoxic or ischemic processes; neurotrauma; metabolically induced neurological damage; sequelae from cerebral seizures; hemorrhagic stroke; secondary neurodegenerative disease (metabolic or toxic); Alzheimer's disease, other memory disorders; or vascular dementia, multi-infarct dementia, Lewy body dementia, or neurodegenerative dementia.

3. The method of claim 2, wherein said administration of said compound is provided at a dosage of about 0.1–6 mg/day.

4. The method of claim 3, wherein said disease is Parkinson's disease.

5. The method of claim 4, wherein said compound is the dihydrochloride.

* * * * *